US012618838B2

(12) United States Patent
Rojas et al.

(10) Patent No.: US 12,618,838 B2
(45) Date of Patent: May 5, 2026

(54) SINGLE DOMAIN VHH ANTIBODIES AGAINST SARS-CoV-2 VIRUS

(71) Applicant: UNIVERSIDAD AUSTRAL DE CHILE, Valdivia (CL)

(72) Inventors: Alejandro Rojas, Valdivia (CL); Guillermo Valenzuela, Valdivia (CL); Ronald Jara, Valdivia (CL); Johanna Himelreichs, Valdivia (CL); Constanza Salinas, Valdivia (CL); Teresa Pinto, Valdivia (CL); Natalia López, Madrid (ES); Yorka Cheuquemilla, Valdivia (CL); Alexei Cuevas, Valdivia (CL); Zaray Miranda, San Jose (CR); Benjamín Uberti, Valdivia (CL); Ananda Muller, Basseterre (KN)

(73) Assignee: UNIVERSIDAD AUSTRAL DE CHILE, Valdivia (CL)

( * ) Notice: Subject to any disclaimer, the term of this patent is extended or adjusted under 35 U.S.C. 154(b) by 518 days.

(21) Appl. No.: 18/055,589

(22) Filed: Nov. 15, 2022

(65) Prior Publication Data

US 2024/0067705 A1 Feb. 29, 2024

Related U.S. Application Data

(63) Continuation of application No. PCT/IB2021/054171, filed on May 14, 2021.

(60) Provisional application No. 63/025,534, filed on May 15, 2020.

(51) Int. Cl.

| | |
|---|---|
| *G01N 33/569* | (2006.01) |
| *A61P 31/14* | (2006.01) |
| *C07K 16/104* | (2026.01) |
| *C12N 15/10* | (2006.01) |
| *G01N 33/68* | (2006.01) |
| *C07K 1/14* | (2006.01) |

(52) U.S. Cl.
CPC ........ *G01N 33/56983* (2013.01); *A61P 31/14* (2018.01); *C07K 16/104* (2026.01); *C12N 15/1086* (2013.01); *G01N 33/6854* (2013.01); *C07K 1/14* (2013.01); *C07K 2317/52* (2013.01); *C07K 2317/565* (2013.01); *C07K 2317/569* (2013.01); *G01N 2333/165* (2013.01); *G01N 2469/10* (2013.01)

(58) Field of Classification Search
CPC ......... G01N 33/56983; G01N 33/6854; G01N 2333/165; G01N 2469/10; A61P 31/14; C07K 16/1003; C07K 1/14; C07K 2317/52; C07K 2317/565; C07K 2317/569; C07K 2317/22; C12N 15/1086
See application file for complete search history.

(56) References Cited

U.S. PATENT DOCUMENTS

| | | |
|---|---|---|
| 2009/0238829 A1 | 9/2009 | Silence et al. |
| 2013/0332133 A1 | 12/2013 | Horn et al. |
| 2014/0165234 A1 | 6/2014 | Dietrich et al. |

OTHER PUBLICATIONS

African Journal of Biotechnology, 10(79):18294-18302, 2011 (Year: 2011).*
J. Immunol. Methods, 251(1-2): 137-149, 2001 (Year: 2001).*
Hussain, et al., "Structural variations in human ACE2 may influence its binding with SARS-CoV-2 spike protein", Journal of Medical Virology, 2020, 92:1580-1586.
Uniprot Submission A0A3D4Jsx5_9FLAO "Transposase" Jan. 16, 2019 [online] [Retrieved Sep. 22, 2021] Retrieved from the internet: <URL:https://www.uniprot.org/uniprot/A0A3D4JSX5>.
International Search Report issued in International Application No. PCT/IB2021/054171, Nov. 9, 2021, 5 pages.
Written Opinion issued in International Application No. PCT/IB2021/054171, Nov. 9, 2021, 5 pages.

* cited by examiner

*Primary Examiner* — Nelson B Moseley, II
*Assistant Examiner* — Josephine K Darpolor
(74) *Attorney, Agent, or Firm* — HSML P.C.

(57) ABSTRACT

The invention provides a set of novel Single domain VHH antibodies against SARS-CoV-2 (SEQ ID No 1-6) and their use to detect and neutralize the wild type virus.

14 Claims, 2 Drawing Sheets

Specification includes a Sequence Listing.

| VHH | Dot blot | Pos. |
|---|---|---|
| W5 | | ++ |
| W23 | | +++ |
| W25 | | +++ |
| C- | | – |
| C+ | | +++ |

SINGLE DOMAIN VHH ANTIBODIES AGAINST SARS-CoV-2 VIRUS

FIELD OF THE INVENTION

The invention relates to a set of single domain VHH antibodies against SARS-CoV-2 and their use in detection, diagnostic, neutralization and therapies against the wild type SARS-CoV-2 virus and its variants.

SEQUENCE LISTING

The present application is being filed along with a Sequence Listing in electronic format. The Sequence Listing is provided as a file entitled Sequence_Listing_20898.0006 USW1.xml, created on Nov. 14, 2023, which is 18.5 bytes (about 19 KB) in size. The information in the electronic format of the Sequence Listing is incorporated herein by reference in its entirety.

STATE OF THE ART

Coronavirus disease 2019 (COVID-19) is the name given to the illness caused by the SARS-CoV-2 infection, a novel coronavirus identified in China and related to pneumonia, that constitutes an unprecedented threat for health and economic systems. Many months have passed since it was first reported and we are still continuously learning about the virus and the associated clinical manifestations, its clinical implications, and possible treatments. By the end of April 2020, over three million people have been infected and more than two hundred thousand have died worldwide, reinforcing the urgent need for better diagnostics and treatment procedures. Currently, there are no vaccines or drugs that can effectively contain the pandemic, and as a result, non-pharmacologic public health measures such as social distancing, border closures, and lockdowns have been enforced globally to flatten the curve and avoid the collapse of health systems. Genetic studies determined that the pathogen responsible for this outbreak belongs to the genus beta-coronavirus, sub-genus sarbecovirus, and the family coronaviridae. It has high sequence homology with the bat coronavirus RaTG13, providing evidence that the new virus may have originated in bats. There are eight coronaviruses associated with human disease: HKU1, hCoV-0043, hCoV-NL-63, hCoV-229E, and the pandemics SARS-CoV-1, MERS and SARS-CoV-2. The SARS-CoV-2 sequence contains 29903 bp, which includes 14 open reading frames (ORFs) coding for the replicase ORF1ab, spike (S), envelope (E), membrane (M) and nucleocapsid (N) structural proteins, and several non-structural (nsps) and accessory proteins. The glycoprotein spike (S) on the surface of the virus is responsible for the attachment and invasion of host cells. The spike is a highly glycosylated trimeric class I fusion protein and contains two subunits, S1 and S2. CryoEM studies showed that it remains in a metastable pre-fusion conformation with a hinge-like movement of the S1 subunit, which binds to the host cell receptor. After attachment, S1 sheds and leaves the S2 subunit in a stable post-fusion conformation. The latter mediates membrane fusion and is responsible for the invasion of the host cell.

The angiotensin-converting-enzyme 2 protein (ACE2) appears to be the entryway to the host, as the SARS-CoV-1 spike binds to this receptor, the virus requires priming proteolysis by the TMPRRS2 serine protease, which attacks a furin-like cleavage site on the S protein. The conformational change then stabilizes the complex, allowing the virus to infect the host cell. The presence of ACE2 was confirmed in different tissues, which can be related to some clinical manifestations of COVID-19; some of them already have in-vitro proof of infection by SARS-CoV-2. This mechanism mediated by S glycoprotein highlights the importance and antigenic properties of this protein as a target for the development of therapies such as neutralizing antibodies and vaccines. Isolation of specific antibodies could be used for the development of an effective diagnostic and therapeutic arsenal against the virus.

Some naturally occurring antibodies lack light chains, known as single-domain antibodies (HCAb, Heavy Chain only Antibodies). They are derivates of IgG and occur in the entire Camelidae family. The camelid family comprises of camels, dromedaries, llamas, vicuñas, guanaco, and alpacas. The antigen-binding fragment of an HCAb contains a single variable VHH domain consisting of 3 hypervariable regions (CDR). The target-specific VHH derived from camelid HCAbs are obtained after immunization with the target protein, plus adjuvant. Our platform has developed an improved procedure for VHH production using alpacas as a donor species. To isolate the genetic sequences of the target-specific VHH produced after immunization, we must first isolate the peripheral B-lymphocytes to obtain total RNA, followed by cDNA preparation to finally amplify the VHH region. The cDNA fragment encoding the VHH is as short as 360 nt, and up to ~$3\times10^6$ single clones can be obtained in a bacterial display library from 120 mL of blood. We used a bacterial display system to clone the full single VHH. Here, we have obtained and selected a set of VHH against the Spike RBD domain of SARS-CoV-2.

Single Domain VHH Antibodies

The target-specific VHH derived from HCAbs of camelids are generally rapidly obtained after immunization with the target protein plus adjuvant. Analysis of the VHH structure reveals how the hypervariable regions are projected in loops outside of the core structure. To isolate the genomic sequences of the target-specific VHH, first peripheral B-lymphocytes must be obtained to isolate total RNA, followed by cDNA preparation to finally amplify the VHH region from gene V of the repertoire. The fragment encoding the VHH in gene V is as short as 360 nt long. VHH sequences are cloned in a Bacterial display vector, thus, after the transformation of the competent bacteria. The bacterial display technology allows VHH to be expressed on the surfaces of bacterium and, therefore, expressing the VHH of interest allowing the affinity purification. The final isolated VHH are recombinantly expressed in bacteria and their binding abilities can be characterized by ELISA and quantitative biochemical parameters such as ITC. VHH are then produced in a renewable and economical manner. Further advantages of VHH are their small size, they can be humanized, their stable structure and behavior in aqueous solutions, their specific and high-affinity binding to a single target protein and their natural production by camelids. Therefore, VHH are the best tools available today for affinity-based diagnostics and therapies.

Advantages of Single Domain VHH Antibodies

Here, we summarise the advantages and uses of VHH in detail.

Purification VHH purification is simple compared to any other antibody source. They are often expressed linked to an affinity tag, such as 6× histidine tags, to allow affinity purification. Enrichment is often set up in the bacterial periplasm where the oxidizing environment allows the formation of proper disulfide bonds. Several milligrams can be isolated from one liter of culture and the recombinant isolated VHH can be further isolated by standard biochemical techniques.

Stability

VHH are small and compact polypeptides and they are often expressed in the periplasm of bacteria. They are very stable at high temperatures, starting at 6° C. compared to human VH, and they are also resistant to denaturing chemical agents. Furthermore, molecular engineering of the VHH structure has shown that stability increases when introducing a cysteine at position 54 and 78 to form an extra disulfide bond. Interestingly, the resulting super stable VHH is also more resistant to proteases such as pepsin or chymotrypsin.

Immune Invisibility

VHH can be used as therapeutic bullets against tumors, pathogens, and chronic diseases, however, as foreign proteins they could trigger an immune response themselves. Fortunately, the small size, rapid clearance from the blood, and high homology to the human variable region of the heavy chain VH make them little immunogenic. Only a few amino acids differ between VHH and the human VH, the substitution camelid amino acids for human amino acids has been used to humanize camelid VHH and make them even safer for therapies.

Accessibility

VHH are strict monomers, their affinity for substrates depends on the projection of the three hypervariable loops. In consequence, VHH tent to interact with cavities of the spatial structure of polypeptides, but not efficiently with peptides. For instance, several identified VHH directly block active enzyme sites. Some VHH can even cross the blood-brain barrier by transcytosis and form partly bispecific antibodies used for therapeutic approaches. Finally, the molecular accessibility impacts access to macromolecular complexes.

Use of single domain VHH antibodies Diagnostics Single domain VHH antibodies are a superior tool for diagnostics. Their unlimited capacity of in vitro production makes VHH more reliable than conventional antibodies and independent of batch preparation or animal serum limitations. VHH can be produced as a protein fused to reporter peptides or proteins for direct staining or visualization, including affinity tags (Flag, HA, V5 and cMyc), fluorescent proteins (GFP, RFP, etc), and enzymes for colorimetric measurements such as horseradish peroxidase (HRP). For instance, ELISA assays can be improved by using VHH for either specific immobilization or detection using a specific VHH coupled to horseradish peroxidase (HRP).

Today, the best chances for cancer survival is earlier detection and opportune surgery. Thus, in vivo detection based on VHH is one of the most promising future technologies to fight cancer.

Therapies

Several VHH have been developed in the context of different experimental therapeutic applications against different viruses: HIV, Hepatitis B virus, influenza virus, Respiratory Syncytial virus, Rabies virus, FMDV, Poliovirus, Rotavirus, and PERVs. Remarkably, VHH can neutralize HIV infection; cell to cell spread has been inhibited using HIV isolated from patients. Due to the low immunoreactivity of VHH in humans, they can be injected into patients with very little or no secondary effects. To make them more efficient and specific, VHH can be linked to produce bivalent, multivalent, and/or multispecific VHH, or combined with other VHH or circulating proteins such as albumin to increase their turn over and therapeutic effectiveness. Rabies virus causes lethal brain infection in people. Soon after exposure anti-rabies prophylaxis is provided with plasma-derived immunoglobulins and vaccines. Often, this occurs directly after the attack of an animal that could be infected. Anti-rabies VHH can significantly prolong survival or even completely heal the disease in animal models. Respiratory Syncytial Virus, RSV, is one of the major causes of hospitalization in children, every year more than 1.9 million children under one year of age are infected, and there are over 0.3 million children under five years of age that are hospitalized. No current therapy is available against RSV. However, trivalent VHH-based therapy is in phase II clinical trials. The absolute novelty of the RSV therapy developed by Ablynx, ALX-0171, is the direct neutralization of the virus in the lung of infected experimentation animals. The VHH is administered by nebulization and it reduces the virus titer by 10.000 times. VHH are also used for immunotherapies against cancer.

Covid-19 and Single Domain VHH Antibodies

Infection with the 2019 coronavirus CoV variant generates similar symptoms to those of severe acute respiratory syndrome caused by SARS-CoV in the 2002-2003 epidemic. Both viruses shared a highly homologous genetic sequence and the same receptor to enter and infect human host cells: the angiotensin-converting enzyme 2 (ACE2) (Zhao, Y., et al. "Single-cell RNA expression profiling of ACE2, the receptor of SARS-CoV-2. bioRxiv." Preprint. Posted (2020)). For this reason, the virus was named SARS-CoV-2 and in February 2020, the WHO named the infection COVID-19 and it was declared the sixth public health emergency of international concern. According to the report published by the WHO on Apr. 27, 2020, there are 2,878,196 confirmed cases and 198,668 deaths. Researchers are using all their resources to generate rapid therapeutic strategies that neutralize the virus and prevent infection to spread.

The virus neutralizing VHHs prevent the entry of the virus by blocking its binding to the receptor. The pathogenic Middle East respiratory syndrome coronavirus (MERS-CoV) and severe acute respiratory syndrome coronavirus (SARS-CoV-1) enter human cells through the large envelope glycoprotein called spike (S) that binds to the ACE2 receptor. Spike proteins are highly immunogenic and due to their role in infection, they represent a vulnerable target for the development of new therapies. Therefore, the high potency and specificity of antiviral antibodies can be a promising therapeutic tool. VHHs for MERS-CoV and SARS-CoV have been previously described. However, no specific VHHs have been reported for SARS-CoV-2. To date, polyclonal antibodies from recovered SARS-CoV-2-infected patients have been used to treat COVID-19. The VHH obtained and protected in this application are powerful tools in the fight against the SARS-CoV-2 pandemic, they can be applied in detection methods and also in therapeutic methods to neutralize the virus both in vivo and ex vivo.

DETAILED DESCRIPTION OF THE INVENTION

Figures 1, 2:
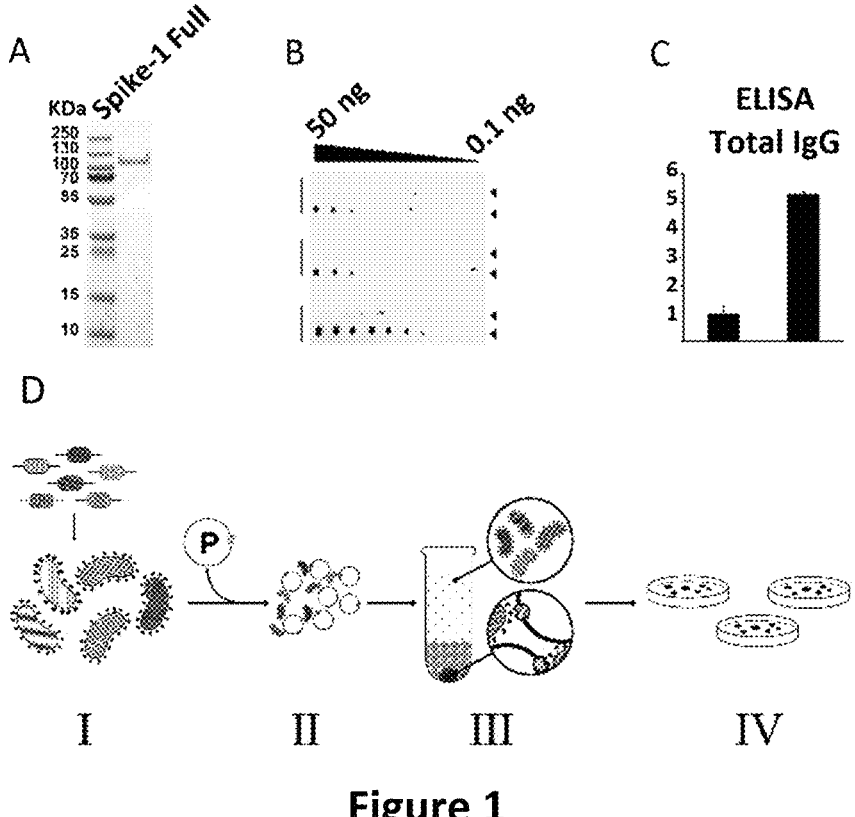
FIG. 1. Immunization of the spike of SARS-CoV-2 and a simple density gradient method for the selection of VHH. (a) SDS-Page to ensure protein integrity of full-length spike of SARS-CoV-2 before immunization. (b) Evaluation of the alpaca's immune response by dot blot. Image shows the reaction to decreasing amounts of Spike (lower row) and bovine serum albumin (upper row, negative control) using a preimmunization control (upper membrane), and after one immunization (1 week, middle membrane), or two immunizations (3 weeks low membrane) with full-length SARS-CoV-2 spike, using alpaca serums as a primary antibody source followed by an anti-camelid IgG-HRP secondary antibody. (c) ELISA before and 3 weeks after the second immunization, n=4, error bars indicate standard deviation statistic t-test, **P≤0.005. (d) Schematic representation of novel protocol for isolation of VHH using density gradient separation: The bacterial display library (I) expressing the VHH on the surface of bacteria is briefly incubated (II) with conventional sepharose beads coated with the antigen of interest. Directly after the mixture is deposited on a Ficoll density gradient conic tube (III) and centrifuged at 200 g for 1 min, the beads drive through the sequential density gradient selection to the bottom of the tube with the bacteria expressing specific VHH, while unbound bacteria remain on the surface of the gradient. The beads are then resuspended, and bacterial clones are isolated (IV, agar plate incubations).
FIG. 2. Immunodetection of Spike—SARS-CoV-2 in a 0.2 μm pore—size nitrocellulose membrane with the VHHs of invention W25, W23 and W5 as the primary antibody, followed by mouse anti-Myc and goat anti mouse IgG coupled to HRP. Negative and positive control are also included.

The invention provides single domain VHH antibodies against the receptor-binding-domain (RBD) domain of SARS-CoV-19 Spike protein.

Despite the worldwide efforts to control COVID-19 progression into a severe acute respiratory syndrome and its impact on health systems, the situation remains critical. Effective diagnostics, treatment, and prophylactic measures in terms of cost, time, and labor are required to meet the worldwide demand: recombinant antibodies such as alpaca VHH could contribute to these requirements. Here, we describe VHH against the receptor-binding-domain (RBD) domain of SARS-CoV-2 Spike protein.

The inventors obtained single domain VHH antibodies that specifically recognize Spike of SARS-CoV-2, both nucleotide and amino acid sequences of the VHH, are shown in the SEQ ID No. 1 to 6. The CDR sequences are shown in SEQ ID No. 7 to 15.

The invention was developed using the Spike protein as the purified antigen. The alpaca was immunized and further single domain VHH antibodies were cloned from periferic lymphocited and further characterised.

The VHH against the Spike protein of SARS-CoV-2 according to the invention comprises 3 CDR having at least a 90% identity with the aminoacidic sequence according to SEQ ID No 7, 8 and 9.

In an embodiment of the invention, the VHH has an aminoacidic sequence having at least a 90% identity with SEQ ID No 2, 4 or 6.

In an embodiment of the invention, the VHH is codificated by a nucleotidic sequence having at least a 90% identity to SEQ ID No 1, 3 or 5.

In a further embodiment of the invention, the VHH comprises 3 CDR having an aminoacidic sequence according to SEQ ID No 7, 8 and 9.

In a further embodiment of the invention, the VHH comprises 3 CDR having an aminoacidic sequence according to SEQ ID No 10, 11 and 12.

A method for the detection of SARS-CoV-2, wherein a VHH according to claim 1 is used for detecting the presence of the virus in a sample.

The correlationship between the sequence numbers and the fantasy number for the VHH of invention is described in table 1.

TABLE 1

| Sequence number | | Type | VHH |
| --- | --- | --- | --- |
| SEQ ID No | 1 | Nucleotide | W25 |
| SEQ ID No | 2 | Peptide | W25 |
| SEQ ID No | 3 | Nucleotide | W23 |
| SEQ ID No | 4 | Peptide | W23 |
| SEQ ID No | 5 | Nucleotide | W5 |
| SEQ ID No | 6 | Peptide | W5 |
| SEQ ID No | 7 | CDR1 | W 25 |
| SEQ ID No | 8 | CDR2 | W 25 |
| SEQ ID No | 9 | CDR3 | W 25 |
| SEQ ID No | 10 | CDR1 | W 23 |
| SEQ ID No | 11 | CDR2 | W 23 |
| SEQ ID No | 12 | CDR3 | W 23 |
| SEQ ID No | 13 | CDR1 | W 5 |
| SEQ ID No | 14 | CDR2 | W 5 |
| SEQ ID No | 15 | CDR3 | W 5 |

For the experts working in this area, it will be evident that a VHH that recognizes Spike of SARS-CoV-2 can be useful in diagnosis and therapies of COVID-19.

In therapy, a VHH that recognizes Spike of SARS-CoV-2 can be used to neutralize the virus and to control the disease in an individual. Single domain VHH antibodies can be produced as fusion with the Fc domain of human antibodies, know as MiniBodies. This allows the link between the single domain VHH antibodies and the human immune system to enhance recognition of the virus by the human immune system.

Therefore, the invention also provides a method for the neutralization of SARS-CoV-2, where a VHH according to the invention is used to neutralize the virus. The in vivo neutralization of the virus allows to control the disease in an individual.

In a preferred embodiment of the invention, the VHH used in the neutralization method is humanized. In another embodiment of the invention, the VHH is bound to a carrier molecule, such as antibodies fusion, human Fc fragment, polyethylene glycol, sialic acid polymers, beta carboxyterminal peptides, albumin or albumin binding peptides and others. Optionally, the one or more VHH according are bound to an human Fc fragment to increase circulatory time and link the immune response of the host.

In diagnosis or virus detection in humans and animals, a VHH that recognizes Spike of SARS-CoV-2 can be used in any technique available, for example in ELISA, immunoblotting, immunohistochemistry, immunoprecipitation, lateral flow test, agglutination in latex, cytometry based studies, Cytometric Bead Array (CBA) and others.

The specificity of an antibody, and of a VHH, is given by the structural complementarity between the antibody combining site and the antigenic determinant. The antibody combining sites are hypervariable regions also know as complementarity-determining regions (CDRs). VHH have three CDRs, so the specificity of each VHH—produced by this invention—is given by its 3 CDRs. Typically, the CDRs can be identified by analyzing the DNA or protein sequence of the antibody or VHH in an appropriate computational system, there are several state of the art systems available. Therefore, to identify the 3 CDRs of the VHH sequences SEQ ID No. 1 to 6 would be a routine procedure for an expert in the field.

It will also be evident that since the specificity of VHH is given by their CDRs, the VHH from this invention can have changes in their "framework region", or "FR" (the name of the amino acid sequences inserted between the CDRs). Therefore, a VHH produced by the invention is defined as a VHH with the same CDRs of the VHH of SEQ ID NOS: 1-6 Equally, these VHH can be defined as a VHH with at least 90% identity with the 3 CDR sequences of a VHH selected from the group contained in SEQ ID NOS: 1-6.

Additionally, the invention comprises structures formed by linking the scFv and/or the VHH of the invention to the Fc fragment of the desired species (minibody), keeping their specificity, binding properties and activity.

EXAMPLES

Example 1. The Simple Density Gradient Method of the Invention and its Use to Obtain VHH Against the Spike Protein of SARS-CoV-2

First, the inventors obtained the protein Spike of lyophilized SARS-CoV-2 raised in a baculovirus expression system. Previous to immunization, the protein integrity of Spike was tested by SDS-Page and Coomassie staining (FIG. 1a). An alpaca called Buddha (FIG. 1b) was immunized two times with 100 μg of the full Spike protein. The immune response of the alpaca's serum before immunization unveiled a fortunate basal cross-reaction against Spike protein. Then, after the second immunization, it was observed a significant increase of IgG antibodies in the alpaca's serum in a rapid qualitative manner by Dotblot analysis, immobilizing the epitope to a nitrocellulose membrane and using alpaca serum as a source of primary antibodies (FIG. 1c). Also, the inventors checked the increase of IgG antibodies—analytically and comparatively—by ELISA using the full Spike protein immobilized on the ELISA plate and using the alpaca serum as a source of primary antibodies (FIG. 1d). Thus, the inventors rapidly constructed a bacterial display library consisting of 2.3×10⁶ single VHH clones with 0.7% relegation of the vector.
Immunization and VHH Library Construction The alpaca immunization process followed the protocol "Animal use in research" generated by the Bioethics Committee of the Austral University of Chile. A day before immunization, 5 ml of blood was collected for pre-immune serum tests. For immunization (day 1), 100 μg of full-length Spike protein of SARS-CoV-2 (SINOBiological) was used. The cold lyophilized protein was dissolved in 2 ml adjuvant (Veterinary Vaccine Adjuvant, GERBU FAMA) diluted 1:1 in sterile water and injected subcutaneously in a male alpaca (Vicugna pacos). A total volume of 4 ml was injected in four different locations in the alpaca. A 5 ml blood sample was collected seven days after the first immunization. On day 14, the alpaca was immunized again with 100 μg Spike, and on day 15, a sample of 120 ml of blood from the jugular vein was collected in tubes containing 3.8% sodium citrate as an anti-coagulant. Uncoagulated blood sample was mixed with the same volume of HBSS medium without calcium (Gibco), divided into aliquots of 10 ml, and 5 ml of Ficoll-Paque Premium (GE Healthcare) were added on top of each aliquot in 15 ml sterile Falcon tubes. After centrifugation (1.200×rpm, 80 min, RT), the PBMC fraction was recovered from the interphase, washed twice in HBSS by centrifugation (3.500×rpm, 10 min), resuspended in 4 ml of sterile PBS 1× (phosphate buffered saline Gibco). RNA extraction and cDNA production were performed using the commercial RNeasy Mini Kit (Qiagen) and QuantiTect Reverse Transcription Kit (Qiagen) respectively. Approximately 2 μl of each synthesized cDNA were used as a template in a total PCR reaction volume of 50 μl with oligonucleotides CALL001 (5'-GTC CTG GCT CTC TTC TAC AAG G-3') and CALL002 (5'-GGTACGTGCTGTT-GAACTGTTCC-3') (Conrath K E, Lauwereys M, Galleni M, Matagne A, Frere J M, Kinne J, Wyns L, Muyldermans S. Beta-lactamase inhibitors derived from single-domain antibody fragments elicited in the camelidae. Antimicrob Agents Chemother. 2001 October; 45(10):2807-12. doi: 10.1128/AAC.45.10.2807-2812.2001). The amplified fragments of ~0.6 kb, corresponding to VHH-CH2 domains, and ~0.9 kb, corresponding to conventional VH-CH1-CH2 domains, were separated in a 1.2% (w/v) low melting agarose gel and the ~0.6 kb band was purified (QIAEXII Gel Extraction kit, Qiagen). This fragment was used as a template in a second PCR reaction with oligonucleotides VHH-Sfi2 (5'-GTC CTC GCA ACT GCG GCC CAG CCGGCC ATG GCT CAG GTG CAG CTG GTG GA-3') and VHH-Not2 (5'-GGA CTA GTG CGG CCG CTG AGG AGA CGG TGA CCT GGG T-3') to finally obtain the amplified fragments of ~0.4 kb, corresponding to VHH domains. The amplified VHH fragments were digested with Sfil and Notl (Thermo Scientific) restriction enzymes and ligated into the same sites of purified vector pNeae2 (Salema V, Lopez-Guajardo A, Gutierrez C, Mencia M, Fernández LÁ. Characterization of nanobodies binding human fibrinogen selected by E. coli display. J Biotechnol. 2016 Sep. 20; 234:58-65. doi: 10.1016/j.jbiotec.2016.07.025). Ligations were electroporated in E. coli DH10B-T1 R cells achieving a library size of ~3×10⁶ individual clones, as determined by plating on LB-Chloramphenicol agar plates with 2% w/v glucose incubated at 30° C. Less than 0.7% re-ligated vectors were estimated from a control ligation performed in parallel without the DNA insert. Transformed bacteria were scraped from plates and stored at −80 degrees in LB broth with 30% glycerol.

Once the library was obtained, the inventors applied the invention method for the selection of VHH based on a simple density gradient using Ficoll. (FIG. 1e).
Coupling Epitopes to Beads 1 mL of NHS-activated sepharose 4 Fast Flow beads (GE Healthcare) were washed with 2 mL of cold 1 mM HCl immediately before use, then washed 5 times with cold sterile PBS. 200 μg of purified protein in PBS 1× was added to the beads and incubated with rotation overnight. Non-reacted groups on the medium were blocked adding ethanolamine to 0.5 M final concentration. Beads were washed 5 times with PBS 1× and stored at 4° C.
Density Gradient Separation 1 mL of glycerol stock from the library was inoculated in a flask containing 20 mL of LB medium with 25 μg mL-1 chloramphenicol and 2% glucose. The flask was incubated (pre-inoculum) overnight at 37° C. with 200 rpm agitation. The same procedure was repeated with control bacteria transformed with a kanamycin-resistant plasmid (control). The pre-inoculum was pelleted and resuspended in LB medium with 25 µg mL-1 chloramphenicol and then diluted to 0.02 $OD_{600\ nm}$ in 100 ml fresh LB medium with 25 µg mL-1 chloramphenicol without glucose, incubated at 37° C. with 200 rpm agitation until it reached 0.45-0.6 OD 600 nm. IPTG was added to a final concentration of 50 µM to induce protein expression for 3 hours at 30° C. and 200 rpm. $OD_{600\ nm}$ absorbance of the library and control bacteria cultures was measured. 50 mL of both cultures were washed three times with 10 mL of filtered PBS. Centrifugation was always at 3000×g for 5 min. Both cultures were resuspended in a final volume of 10 mL PBSX. 2 ml of library culture and 2 ml control culture was mixed (if final $OD_{600\ nm}$ were the same, if not the volume of control bacteria was adjusted based on OD to ensure an equal amount of bacteria) and incubated with 300 µL NHS beads coupled to epitope protein in a 15 mL conical tube on a rocking platform for 30 min at room temperature. The mixture was added on 6 ml Ficoll (Ficoll-Paque™ PLUS GE Healthcare) in a 15 mL conical tube, centrifuged at 200×g for 1 min. The unbound fraction was discarded (upper fractions), leaving a visible pellet of beads that was resuspended in 4 mL PBS and rotated for 5 min at room temperature. This step was repeated six times. Finally, 1 mL of LB medium was added and incubated for 5 min at room temperature, then 50 µL were plated on LB agar plates with 25 µg mL-1 chloramphenicol and 2% glucose, incubated at 37° C. overnight (>20 hrs recommended).

The bacterial display system expresses VHH on the surface of bacteria fused to an intein protein and a myc tag. Buffer conditions were optimized to extract the VHH-intein fusion from the bacterial membrane and used the bacterial extract directly for binding confirmation to Spike applying two different methods: Dot blot analysis and High-content microscopy. After VHH selection using our simple density gradient protocol based on Ficoll, we obtained~1000 colonies on LB-agar plates from the sepharose-antigen coated fraction. 100 colonies were used to inoculate liquid LB media and further induced for the expression of intein-VHH. Cells were lysed under optimized conditions and the extract was used as a source of VHH as primary antibodies for the secondary binding screening. For dot blot analysis, a negative control of an unrelated protein was applied at the same amount of Spike full length onto nitrocellulose strips. Further, single dot blot strip tests were incubated with the bacterial extracts containing VHH in 12 well-plates. VHH binding to Spike were unveiled by sequential incubation with mouse anti-myc antibody and an anti-mouse HRP-conjugate. Of the first 100 clones, three showed a strong binding capability for full-length Spike in the dot blot analysis W25, W23 and W5 (W25 SEQ ID No. 1 and SEQ ID No. 2 and W23 SEQ ID No. 3 and SEQ ID No. 4, W5 SEQ ID No.5 and SEQ ID No.6).

Example 2. Binding Assay

Dot Blot

Individual colonies from bacteria expressing VHH, W25, W23 and W5, (DH10b strain) obtained from example 1 were inoculated in to 2 mL of LB medium and incubated overnight at 37° C. with 200 rpm agitation. 100 µL of pre-inoculum added to 1.9 mL of fresh LB medium with 25 µg mL-1 chloramphenicol, incubated at 37° C. with 200 rpm agitation until reach 0.45-0.6 $OD_{600\ nm}$. IPTG was added to a final concentration of 50 µM to induce protein expression for 3 hours at 30° C. and 200 rpm. Culture was pelleted and resuspended in 1 mL PBS 1×0.2% TritonX100, sonicated 10 seconds at 40% on ice, then centrifuged at 14,000×g, 30 min, at 4° C. and supernatant was recovered to obtain a total protein extract from each clone. 1 µl of protein SARS-CoV-2 Spike protein (200 ng/µl), and a E. coli total protein extract, as negative control, was spotted within a pre marked grid in to a 0.2 µm pore-size nitrocellulose membrane (Merk Millipore), in parallel an anti histag commercial antibody was used as positive control, due Spike protein used had an 6× histidine tag. The membrane is then left to dry to fix the proteins to it for 30 min at room temperature. Non-specific sites are blocked with blocking solution (PBS-T with 5% bovine serum albumin) for 30 min at room temperature with agitation. Blocking solution is discarded and each membrane is incubated 1 hr at room temperature with agitation with a dilution of 1:10 each clone total protein extract in 5 ml of PBS-T containing 5% BSA, followed by 3×5 min wash with PBS-T. Secondary antibody incubation is done with mouse anti-myc antibody (9B11, Cell Signalling), 1:3000 in TBS-T containing 5% BSA, 1 hr at room temperature, followed by 3×5 min wash with TBS-T. After this, the membrane was incubated with a goat anti-mouse IgG coupled to HRP antibody (Invitrogen), 1:5000 in PBS-T containing 5% BSA, 1 hr at room temperature, followed by 3×5 min washes with PBS-T and developed using ECL reagent. The results are shown in FIG. 2 where a photograph of the dot blot is included. It is appreciated that there was a strong response for the 3 VHH tested.

Figure 3:
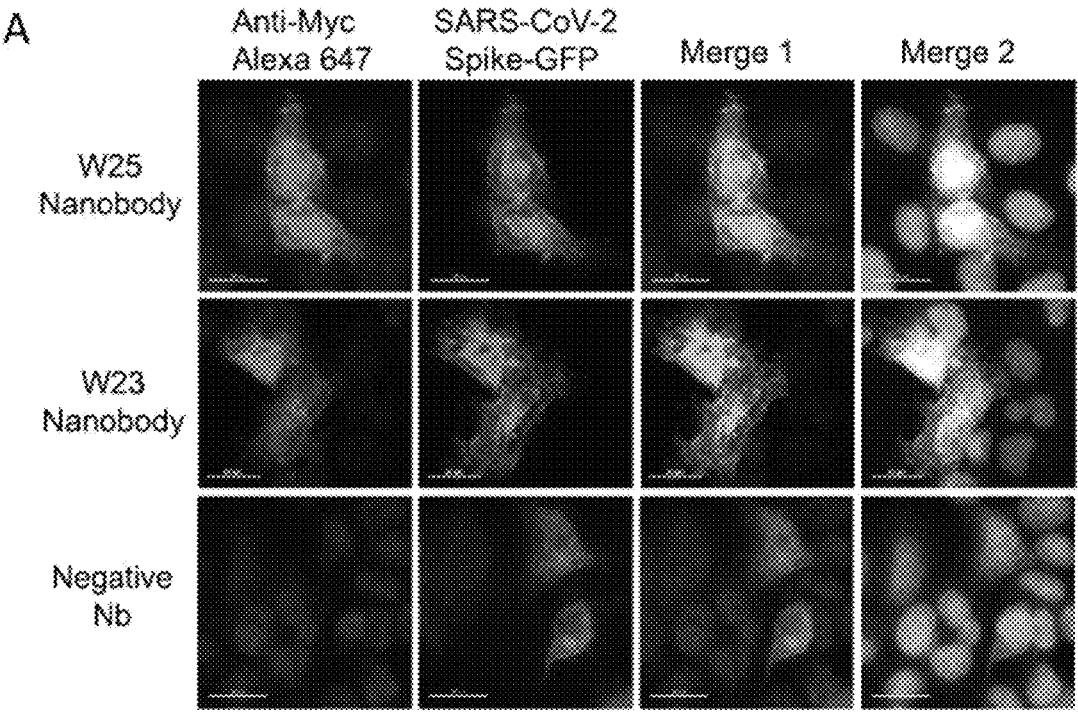
FIG. 3. Dual biochemical and microscopy-based selection of VHH. (a) Immunodetection of Spike-GFP transiently transfected in HeLa cells using total protein extract of selected clones as the primary antibody, followed by mouse anti-Myc (1:3000) and anti-mouse-Alexa 647. The image shows two positive clones (W25 and W23), and an example of a negative VHH the screening assay was performed once, scale bar indicates 20 μm. (b) Representation of how fluorescence intensity graphs were elaborated, measuring fluorescence in green (Spike-GFP) and red channel (VHH) in a cell crossing section. Graphs depict fluorescence intensity of Spike-GFP (continuous line) and VHH (dot line) of a negative control VHH (c), W25 (d) and W23 (e).
Figure 3:
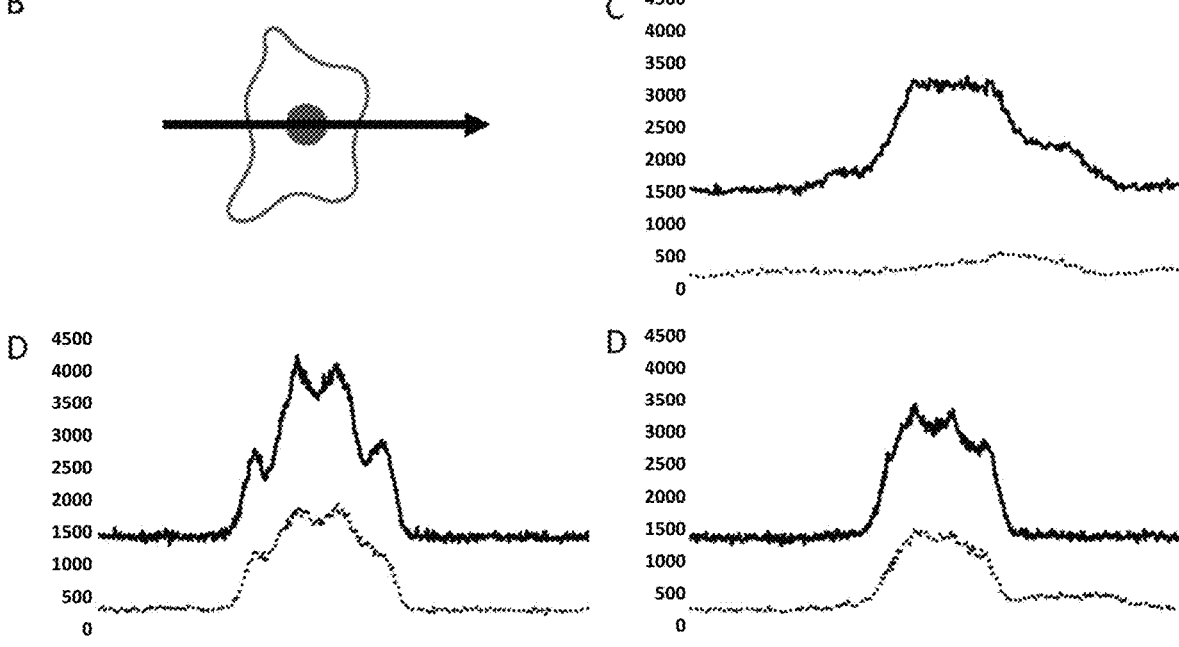

Furthermore, we used high content microscopy as a second confirmation method. Therefore, a single 10 cm-plate was transfected with Spike-GFP for 24 h, and cells were seeded onto 3×96 well-plates. After 24 hours, the cells were fixed, permeabilized, and individual extracts of our 100 selected bacterial display clones were incubated as a source of VHH acting as primary antibodies. VHH are myc-tagged, after incubation with mouse anti-myc antibody and an anti-mouse Alexa647 secondary antibody cells were analyzed by immunofluorescence assays. HeLa cells showed a transfection efficiency of ~20%. In this case, a low transfection rate is desired because it indicates unspecific binding to untransfected cells in the same image. Consistent with the dot blot analysis, the VHH W23 and W25s bound to Spike-GFP expressed under viral natural conditions in human cells (FIG. 3a). We observed colocalization of W23 and W25 to Spike-GFP, while no colocalization was observed with negative control extracts (FIG. 3b). The selected clones were sequenced, the alignment of the amino acid sequences show that both VHH are different and most likely recognize different Spike epitopes. Thus, we showed that rapid secondary screening selections of VHH using bacterial extracts directly from the bacterial display library selected clones using either conventional biochemical methods such as dot blot analysis or high content microscopy immunofluorescence-based assays.

---

The invention claimed is:

1. A VHH against the Spike protein of SARS-COV-2, wherein the VHH comprises a set of three CDRs having aminoacidic sequences selected from the group consisting of: SEQ ID NOs: 7, 8, and 9; SEQ ID NOs: 10, 11, and 12; and SEQ ID NOs: 13, 14, and 15.

2. The VHH according to claim 1 having an aminoacidic sequence of SEQ ID NO: 2.

3. The VHH according to claim 2, wherein the VHH is encoded by a nucleotidic sequence of SEQ ID NO: 1.

4. The VHH according to claim 1 having an aminoacidic sequence of SEQ ID NO: 4.

5. The VHH according to claim 4, wherein the VHH is encoded by a nucleotidic sequence of SEQ ID NO:3.

6. The VHH according to claim 1 an aminoacidic sequence of SEQ ID NO: 6.

7. The VHH according to claim 6, wherein the VHH is encoded by a nucleotidic sequence of SEQ ID NO:5.

8. A method for detecting a SARS-COV-2 virus, comprising detecting a presence of the virus in a sample by an immunoassay using the VHH according to claim 1.

9. The method according claim 8, wherein the immunoassay is an assay selected from the group consisting of ELISA, immunoblotting, immunohistochemistry, and immunoprecipitation.

10. A method for neutralizing a SARS-COV-2 virus, the method comprising neutralizing the virus using wherein the VHH according to claim 1.

11. The method according to claim 10, wherein the neutralizing is performed in vivo, and the neutralizing of the virus allows to control COVID-19 in an individual.

12. The method according claim 11, wherein the VHH is humanized.

13. The method according to claim 10, wherein the VHH is bound to a carrier molecule selected from the group consisting of an antibody fragment, human Fc fragment, polyethylene glycol, sialic acid polymers, beta carboxyterminal peptides, albumin, and albumin binding peptides.

14. The method according claim 13, wherein the VHH is bound to a human Fc fragment.

* * * * *

SEQUENCE LISTING

Sequence total quantity: 19
SEQ ID NO: 1                    moltype = DNA   length = 363

-continued

```
FEATURE           Location/Qualifiers
source            1..363
                  mol_type = genomic DNA
                  organism = Vicugna pacos
SEQUENCE: 1
atggctcagg tgcagctggt ggagtctggg ggaggcttgg tgcagcctgg ggagtctctg    60
agactctcct gtgcagcctc tggaagtatc ttcggaatct atgccgtgca ctggttccgc   120
atggctccag ggaaggagcg cgagtttact gcaggttttg gaagtcatgg tagcacaaat   180
tatgcagctt ccgtgaaggg acgattcacc atgtccagac acaatgccaa gaacacgacg   240
tatctgcaaa tgaacagcct gaaacctgcg gacacggccg tctattactg tcatgcgcta   300
ataaagaatg aacttgggtt ccttgactac tggggccgcg ggacccaggt caccgtctcc   360
tca                                                                  363

SEQ ID NO: 2         moltype = AA  length = 121
FEATURE           Location/Qualifiers
source            1..121
                  mol_type = protein
                  organism = Vicugna pacos
SEQUENCE: 2
MAQVQLVESG GGLVQPGESL RLSCAASGSI FGIYAVHWFR MAPGKEREFT AGFGSHGSTN    60
YAASVKGRFT MSRDNAKNTT YLQMNSLKPA DTAVYYCHAL IKNELGFLDY WGPGTQVTVS   120
S                                                                   121

SEQ ID NO: 3         moltype = DNA  length = 363
FEATURE           Location/Qualifiers
source            1..363
                  mol_type = genomic DNA
                  organism = Vicugna pacos
SEQUENCE: 3
atggctcagg tgcagctggt ggagtctggg ggaggcttgg tgcagcctgg ggagtctctg    60
agactctcct gtgcagcctc tggaaacatc ttcggaatcg ctgccgtgca ctggttccgc   120
aaggctccag ggaaggagcg cgagtttact gcaggttttg gtagtgatgg tagcacaaac   180
tatgcaaact ccgtgaaggg ccgattcacc atctccagag acaatgccaa gaacacgaca   240
tatctgcaaa tgaacagcct gaaacctgag gacacggccg tctattattg tcatgcgcta   300
atcaagaatg aacttggatt ccttgattac tggggccccg ggacccaggt caccgtctcc   360
tca                                                                  363

SEQ ID NO: 4         moltype = AA  length = 121
FEATURE           Location/Qualifiers
source            1..121
                  mol_type = protein
                  organism = Vicugna pacos
SEQUENCE: 4
MAQVQLVESG GGLVQPGESL RLSCAASGNI FGIAAVHWFR KAPGKEREFT AGFGSDGSTN    60
YANSVKGRFT ISRDNAKNTT YLQMNSLKPE DTAVYYCHAL IKNELGFLDY WGPGTQVTVS   120
S                                                                   121

SEQ ID NO: 5         moltype = DNA  length = 363
FEATURE           Location/Qualifiers
source            1..363
                  mol_type = genomic DNA
                  organism = Vicugna pacos
SEQUENCE: 5
atggctcagg tgcagctggt ggagtctggg ggaggcttgg tgcagcctgg ggagtctctg    60
agactctcct gtgcagcctc tggaagtatc ttcggaatct atgccgtgca ctggttccgc   120
aaggctccag ggaaggagcg cgagtttact gcaggttttg gaagtgatgg tagcacaaat   180
tatgcagctt ccgtgaaggg acgattcacc atgtccagag acaatgccaa gaacacgacg   240
tatctgccaa tgaacagcct gaaacctgcg gacacggccg tctattactg tcatgcgcta   300
ataaagaatg aacttgggtt ccttgactac tggggcccgg ggacccaggt caccgtctcc   360
tca                                                                  363

SEQ ID NO: 6         moltype = AA  length = 121
FEATURE           Location/Qualifiers
source            1..121
                  mol_type = protein
                  organism = Vicugna pacos
SEQUENCE: 6
MAQVQLVESG GGLVQPGESL RLSCAASGSI FGIYAVHWFR KAPGKEREFT AGFGSDGSTN    60
YAASVKGRFT MSRDNAKNTT YLPMNSLKPA DTAVYYCHAL IKNELGFLDY WGPGTQVTVS   120
S                                                                   121

SEQ ID NO: 7         moltype = AA  length = 8
FEATURE           Location/Qualifiers
source            1..8
                  mol_type = protein
                  organism = Vicugna pacos
SEQUENCE: 7
GSIFGIYA                                                               8
```

-continued

```
SEQ ID NO: 8          moltype = AA   length = 7
FEATURE               Location/Qualifiers
source                1..7
                      mol_type = protein
                      organism = Vicugna pacos
SEQUENCE: 8
FGSHGST                                                            7

SEQ ID NO: 9          moltype = AA   length = 13
FEATURE               Location/Qualifiers
source                1..13
                      mol_type = protein
                      organism = Vicugna pacos
SEQUENCE: 9
HALIKNELGF LDY                                                     13

SEQ ID NO: 10         moltype = AA   length = 8
FEATURE               Location/Qualifiers
source                1..8
                      mol_type = protein
                      organism = Vicugna pacos
SEQUENCE: 10
GNIFGIAA                                                           8

SEQ ID NO: 11         moltype = AA   length = 7
FEATURE               Location/Qualifiers
source                1..7
                      mol_type = protein
                      organism = Vicugna pacos
SEQUENCE: 11
FGSDGST                                                            7

SEQ ID NO: 12         moltype = AA   length = 13
FEATURE               Location/Qualifiers
source                1..13
                      mol_type = protein
                      organism = Vicugna pacos
SEQUENCE: 12
HALIKNELGF LDY                                                     13

SEQ ID NO: 13         moltype = AA   length = 8
FEATURE               Location/Qualifiers
source                1..8
                      mol_type = protein
                      organism = Vicugna pacos
SEQUENCE: 13
GSIFGIYA                                                           8

SEQ ID NO: 14         moltype = AA   length = 7
FEATURE               Location/Qualifiers
source                1..7
                      mol_type = protein
                      organism = Vicugna pacos
SEQUENCE: 14
FGSDGST                                                            7

SEQ ID NO: 15         moltype = AA   length = 13
FEATURE               Location/Qualifiers
source                1..13
                      mol_type = protein
                      organism = Vicugna pacos
SEQUENCE: 15
HALIKNELGF LDY                                                     13

SEQ ID NO: 16         moltype = DNA   length = 21
FEATURE               Location/Qualifiers
source                1..21
                      mol_type = genomic DNA
                      organism = Vicugna pacos
SEQUENCE: 16
gtcctggctc tcttctacaa g                                           21

SEQ ID NO: 17         moltype = DNA   length = 23
FEATURE               Location/Qualifiers
source                1..23
                      mol_type = genomic DNA
                      organism = Vicugna pacos
SEQUENCE: 17
ggtacgtgct gttgaactgt tcc                                         23
```

-continued

```
SEQ ID NO: 18          moltype = DNA  length = 50
FEATURE                Location/Qualifiers
source                 1..50
                       mol_type = genomic DNA
                       organism = Vicugna pacos
SEQUENCE: 18
gtcctcgcaa ctgcggccca gccggccatg gctcaggtgc agctggtgga                   50

SEQ ID NO: 19          moltype = DNA  length = 36
FEATURE                Location/Qualifiers
source                 1..36
                       mol_type = genomic DNA
                       organism = Vicugna pacos
SEQUENCE: 19
ggactagtgc ggccgctgag gagacggtga cctggg                                  36
```